United States Patent
Samyn et al.

[11] Patent Number: 5,672,859
[45] Date of Patent: Sep. 30, 1997

[54] REPRODUCTION APPARATUS WITH MICROWAVE DETECTION

[75] Inventors: Johan Samyn, Roeselare; Walter Van Loock, Laarne, both of Belgium

[73] Assignee: N.V. Bekaert S.A., Zwevegem, Belgium

[21] Appl. No.: 388,254

[22] Filed: Feb. 13, 1995

[30] Foreign Application Priority Data

| Mar. 4, 1994 | [EP] | European Pat. Off. | 94200555 |
|---|---|---|---|
| Oct. 14, 1994 | [EP] | European Pat. Off. | 94202985 |

[51] Int. Cl.$^6$ .............. G06K 7/10; G06K 7/08; G03G 21/00
[52] U.S. Cl. .............. 235/468; 235/449; 355/201
[58] Field of Search .............. 355/201, 202; 283/902; 324/637, 636; 235/468, 449

[56] References Cited

U.S. PATENT DOCUMENTS

| 4,408,156 | 10/1983 | Veys | 324/58.5 |
|---|---|---|---|
| 4,408,158 | 10/1983 | Brozovich et al. | 324/78 R |
| 4,566,121 | 1/1986 | Samyn | 382/7 |
| 4,566,122 | 1/1986 | Samyn | 382/7 |
| 4,739,377 | 4/1988 | Allen | 355/201 X |
| 4,820,912 | 4/1989 | Samyn | 235/449 |
| 4,956,666 | 9/1990 | Allen et al. | 355/201 |
| 4,980,719 | 12/1990 | Allen et al. | 355/201 |
| 5,128,621 | 7/1992 | Berthaud et al. | 324/639 |
| 5,279,403 | 1/1994 | Harbaugh et al. | 194/207 |
| 5,321,470 | 6/1994 | Hasuo et al. | 355/201 |
| 5,379,093 | 1/1995 | Hashimoto et al. | 355/201 |
| 5,390,003 | 2/1995 | Yamaguchi et al. | 355/201 |
| 5,440,409 | 8/1995 | Sugano et al. | 358/501 |
| 5,481,378 | 1/1996 | Sugano et al. | 358/501 |

FOREIGN PATENT DOCUMENTS

| 0 092 691 | 11/1983 | European Pat. Off. | 235/449 |
|---|---|---|---|
| 0 293 222 | 11/1988 | European Pat. Off. | 235/449 |
| 0 558 759 | 9/1993 | European Pat. Off. | 235/449 |
| 904285 | 8/1962 | United Kingdom | 235/449 |
| 88/08529 | 11/1988 | WIPO | 235/449 |

OTHER PUBLICATIONS

H.W. Simpson, "Copier Document Security", *IBM Technical Disclosure Bulletin*, vol. 17, No. 11, p. 3182 (1975).
Patent Abstracts of Japan, vol. 9, No. 174(p–374), Jul. 19, 1985, abstract of Kouichi Aota, "Preventing Device of Copying Secret Document", Japanese 60–49379, Mar. 1985.
Patent Abstracts of Japan, vol. 12, No. 8, (P–654) Jan. 1988, abstract of Maeno Yorihiko, "Physical Measuring Apparatus For Planar Material", Japanese 62–169041, Jul. 1987.

*Primary Examiner*—Donald T. Hajec
*Assistant Examiner*—Thien Minh Le
*Attorney, Agent, or Firm*—Foley & Lardner

[57] ABSTRACT

A reproduction apparatus (14) for reproducing documents (12) which comprise a base material. The apparatus comprises a platen (10) for forming a scanning area and for positioning the documents (12) on its one side, scanning means (18) for scanning the scanning area, and means for obtaining a relative movement between the scanning means and the documents in order to allow for the scanning. The scanning means (18) comprise a microwave system which is constituted by microwave transceivers (26) arranged in an array such that they can detect the presence of particles (13) which have electromagnetic properties which are substantially different from the electromagnetic properties of the base material and which are incorporated in at least a part of the documents (12), irrespective of the position of the documents (12) on the scanning area.

18 Claims, 5 Drawing Sheets

REPRODUCTION APPARATUS WITH MICROWAVE DETECTION

FIELD OF THE INVENTION

The present invention relates to a reproduction apparatus such as a photocopying apparatus for reproducing documents.

BACKGROUND OF THE INVENTION

The quality of high-resolution color photocopying apparatus has increased to such an extent that illicit reproduction of security documents such as banknotes, shares, cheques, passports, bonds and even credit cards has become easier.

One general solution to the above problem is to provide the security documents with a marking which can not be copied by means of a photocopying apparatus. Documents having the appearance of security documents but without the marking can then be classified as counterfeit.

One of the markings provided by the prior art is an optical marking, since these markings are not completely copied. Wear and surface dammage of the genuine security documents may lead, however, to disappearance of the marking so that genuine security documents themselves risk to be designated as counterfeit.

Another marking provided by the prior art is the incorporation of a thread in the security documents. Examples of apparatus for detecting the presence of such a thread in banknotes, and thus for verifying the authenticity of the banknotes can be found in EP-A-0 092 691 and in U.S. Pat. No. 5,279,403. The material and form of the threads used in security documents is so diversified, that the design of a unique apparatus adapted to detect the threads in all security documents appears to be impossible. Moreover, these apparatus have as a disadvantage that they can only detect counterfeit long after it has occurred.

SUMMARY OF THE INVENTION

It is an object of the present invention to avoid the disadvantages of the prior art.

It is also an object of the present invention to provide for a system which may prevent falsification of security documents.

According to the invention there is provided for a reproduction apparatus, such as a photocopying apparatus, for reproducing documents.

The apparatus comprises a platen for forming a scanning area and for positioning the documents on its one side.

The apparatus further comprises scanning means for scanning the scanning area. The scanning means are positioned on the same or on the other side of the platen. The apparatus also comprises means for obtaining a relative movement between the scanning means and the documents in order to allow for the scanning operation.

The scanning means comprise a microwave system. This microwave system comprises a number of microwave sources for generating microwaves, a number of microwave emitters for emitting microwaves to the scanning area, a number of microwave receivers for receiving microwaves which are reflected and a number of microwave detectors for detecting the reflected microwaves. The number of emitters, the number of receivers and the number of detectors are greater than or equal to the number of sources. The number of emitters and the number of receivers are greater than or equal to the number of detectors. The position and number of the emitters and receivers are such that they can detect the presence of particles having some electromagnetic properties which are substantially different from the corresponding electromagnetic properties of the base material and being incorporated in at least a part of the documents irrespective of the position and size of the documents on the scanning area.

The presence of the particles is detected by their reflecting at least part of the emitted microwaves back and thereby producing a greatly varying reflection signal, whereas in absence of particles the reflection response signal does not vary to such an extent.

The above system has the advantage of resulting in a very fast, almost an instant response, which does not prolong considerably the scanning cyclus. Tests have shown that 1 cm (centimeter) after having passed over the first present particles, a decision can already be taken about the presence of the particles. Such a fast speed response can hardly be reached by means of optical systems.

Other advantages of the above system, particularly in comparison with optical systems, are that the system is insensitive for dust, that the presence of any particles can hardly be hidden by placing one or another sheet between the sensor and the security documents and that a high level of detectability is maintained despite any aging, crumpling or soilage of the security documents.

Microwave systems for detecting the presence of particles in a base material with substantially different electromagnetic properties are already known in the art (see e.g. U.S. Pat. No. 4,408,156; U.S. Pat. No. 4,566,121; U.S. Pat. No. 4,566,122 and U.S. Pat. No. 4,820,912), but are not appropriate for the above purpose of functioning in a reproduction machine and of scanning an area which is both in length and in width much larger than the wavelength of the microwaves.

Within the context of the present invention:

- the terms 'reproduction apparatus' comprise a black and white copying apparatus, a high resolution true color photocopying apparatus, and also a scanning apparatus for digitizing pictures for further treatment by a computer;
- the term 'platen' is used for every support structure transmitting waves and light, where the documents to be copied can be positioned; it can be flat or cylindrical;
- the terms 'scanning area' refer to the whole area which can be scanned; it determines the maximum size of the documents which can be copied in one time;
- the term 'scanning' includes the so-called pre-scanning for checking the position and dimension of the documents and the one or more scanning cycli for the copying step itself;
- the terms 'relative movement' point to the movement between the document and the scanning means; two different embodiments are possible: a photocopying apparatus with a movable platen and a photocopying apparatus with a fixed platen;
- the terms 'microwave source' designate a microwave oscillator which generates microwaves; examples of microwave sources are a Gunn-diode, a high electron mobility transistor and a metal semiconductor field effect transistor;
- the terms 'microwave emitter' and 'microwave receiver' include simple antenna structures such as half wave dipoles, quarter wave dipoles, microstrip patches and waveguide apertures;

the terms 'microwave detector' include a Schottky diode;

the terms 'particles having some electromagnetic properties which are substantially different from the electromagnetic properties of the base material' refer to any small-sized materials which can be incorporated in the base material of security documents and which have a dielectric constant $\epsilon$, a magnetic permeability $\mu$, or an electric resistivity $\rho$ differing substantially from the $\epsilon$, $\mu$ or $\rho$ of the base material; examples of such particles are electrically conducting stainless steel fibres being incorporated in a base material of paper or plastic;

the term 'reflecting' also includes scattering back which does not necessarily occur in the same direction as the emission of microwaves.

The source, emitter, receiver and detector are not necessarily physically distinct from each other. Following embodiments are possible:

the function of generating and detecting microwaves is carried out by one device, a so-called self-detecting diode;

the function of emitting and receiving microwaves is carried out by a single antenna or by one simple aperture in a wave guide;

the function of receiving and detecting microwaves is carried out by a single detector which receives the reflected microwaves.

Preferably the microwave system comprises only one source and a plurality of emitters, receivers and detectors. This system combines the advantages of being simple and light-weight and of providing a high signal to noise ratio which is e.g. higher than 20 dB or higher than 25 dB.

Generally, the means for guiding the microwaves may include following structures: a hollow wave guide made of metal or of metallised plastic, planar structures such as microstrips, striplines and slotlines, and coaxial transmission lines.

For reasons of further reducing the weight and increasing the compactness, the means for guiding the microwaves are preferably constituted by the above mentioned planar structures.

In this way a microwave system can be obtained with a weight which is less than 100 g, preferably less than 80 g and most preferably less than 50 g. It is hereby understood, however, that such low weights are not excluded if a hollow wave guide is used.

The copying apparatus according to the present invention may further comprise means for processing the signal produced by the reflected microwaves. These processing means can be digital or analog or a combination of both. The apparatus also comprises means for generating:

an 'on' signal in case the presence of particles is detected in the base material of the documents; and an 'off' signal in case the presence of particles is not detected in the base material of the documents; (or vice versa).

In case of the 'on' signal, copying will be prohibited or only a black copy will be given or another copying resolution will be used or copying will be done in other colors, and so counterfeit will be prevented.

In case of the 'off' signal, the conventional copying process will proceed.

In a particular embodiment of the invention, hereinafter referred to as third embodiment, the microwave system further comprises for each emitter a switching diode so arranged that it can short-circuit the corresponding emitter.

In another embodiment of the invention, hereinafter referred to as fourth embodiment, the emitters and receivers are arranged as resonating structures responding to one single frequency. Within the context of the present invention, the terms 'resonating structure' not only mean structures responding to a predetermined frequency range but also structures giving a response as soon as the frequency exceeds a predetermined under limit.

In yet another embodiment of the invention, hereinafter referred to as fifth embodiment, each of the emitters responds to one single resonant frequency which is different from the resonant frequency of the emitters. The microwave system further comprises means for electronically tuning the frequency of the generated microwaves so that by generating microwaves with changing frequency each emitter becomes sequentially active.

In still another embodiment of the invention, hereinafter referred to as sixth embodiment, the array of emitters loads a resonating structure like a cavity resonator.

In a seventh embodiment, the microwave system comprises two transmission systems, one transmission system for transmitting the generated microwaves and reflected microwaves in one polarization, and another transmission system, which is decoupled from the first transmission system and which is adapted for transmitting reflected microwaves in a polarization system which is different from or equal to the polarization system of the generated microwaves.

Finally, in an eighth embodiment one microwave source and a plurality and equal number of emitters, receivers and detectors is used. The detectors are positioned close to each emitter.

BRIEF DESCRIPTION OF THE DRAWINGS

The invention will now be explained into more detail with reference to the accompanying drawings wherein FIG. 1 gives an upper view of banknotes lying on a glass platen of a copying apparatus.

DESCRIPTION OF PREFERRED EMBODIMENTS OF THE INVENTION

The idea behind the present invention is based on the following principle: instead of developing systems for detecting possible counterfeit documents long after the actual counterfeit has occurred and thus long after the counterfeiting bird is flown, the present system aims at preventing counterfeit, or at least at making it counterfeiters more difficult at the time they try to counterfeit.

The present invention provides for a system which prevents a certain class of documents, hereinafter called 'security documents' to be copied, e.g. by means of a high-resolution color copying apparatus. The terms 'security documents' cover all documents such as banknotes, shares, cheques, passports, bonds and even credit cards or the like, having a base material with electromagnetic properties some of which differ sensibly from the corresponding electromagnetic properties of any particles to be incorporated in the base material, e.g. a base material which is substantially electrically non-conductive. Examples of such base material are paper and plastic.

In order to prevent the copying of the security documents, these documents should contain in at least a part a number of particles such as stainless steel fibres. For reasons of simple mix with the base material and for other reasons which will become clear hereunder, the stainless steel fibres are preferably spread over the complete document.

Usually the documents comprise less than 5% by weight of stainless steel fibres, e.g. less than 1% by weight or less than 0.5% by weight. The stainless steel fibres are randomly distributed in the documents.

The stainless steel fibres have a length which is smaller than 40 mm, preferably smaller than 20 mm, and most preferably smaller than 10 mm, e.g. 3 to 6 mm.

The reason of the limitation of the length is to allow an easy mix with the base material and to avoid a considerable influence of the stainless steel fibres on the visual aspects of the documents.

The stainless steel fibres function as an electrical dipole. They can even give a resonant reflection. The fibres have, despite a low concentration and even with low microwave densities, a relatively high reflection rate. This means that the consumed microwave energy can be kept very small, a source power of e.g. about 5 mW is sufficient, which means that an additional electrical load is not put upon the reproduction apparatus.

The microwave radiation level caused by the present microwave system is very limited, which means that no potential health risks are associated with the system.

The stainless steel fibres have a diameter which is smaller than 50 micrometer and which is preferably in the range of 2 to 25 micrometer, also for reasons of visual aspects of the documents.

The presence or absence of the stainless steel fibres will be detected by means of a microwave system. Microwave frequencies may range from 1 to 50 GHz (GigaHertz), but the length and the diameter of the stainless steel fibres determines the optimal frequency.

For stainless steel fibres having a length between 2.5 and 10 mm, e.g. about 6 mm, a proper frequency range is between 20 and 30 GHz, e.g. about 25 GHz.

With respect to the diameter of the stainless steel fibres an optimal frequency is obtained if the penetration depth of the microwaves as a consequence of the skin effect is equal to half the diameter.

Due to the high frequencies between 20 and 30 GHz, very fast detector responses are possible.

Figure 1:
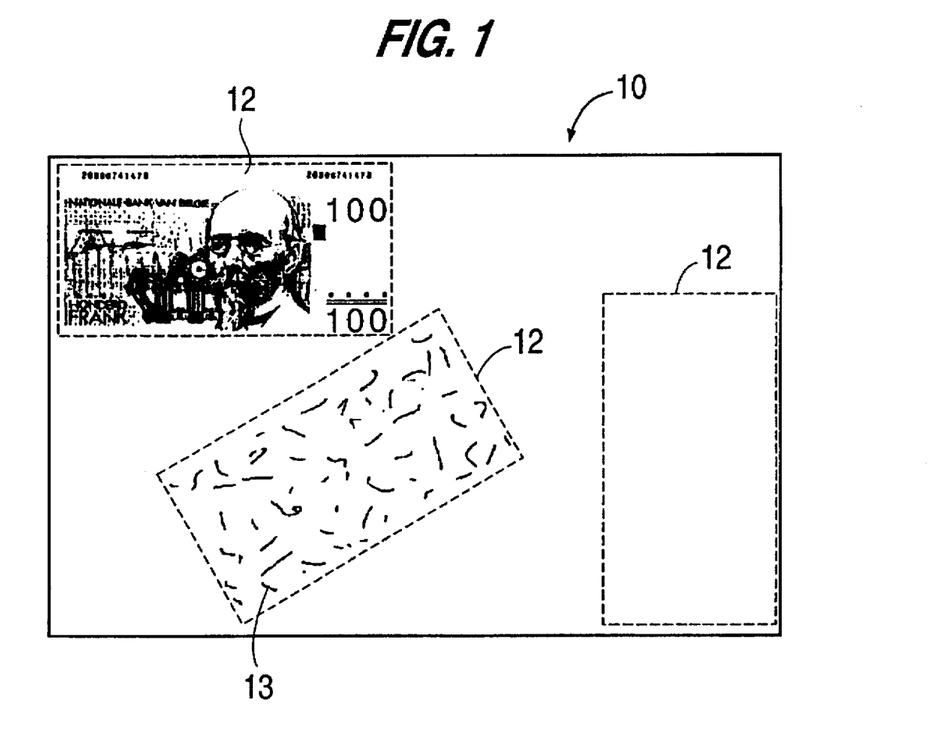

FIG. 1 illustrates a platen glass 10 of a photocopying apparatus forming the scanning area. The thickness of such a platen glass 10 usually ranges from 2 to 6 mm, e.g. from 3 to 5 mm. Documents such as banknotes 12 lie on the platen glass 10 and comprise stainless steel fibres 13 randomly distributed over the whole volume of the banknotes 12.

Assume, for example, that the surface of the scanning area is equal to the surface of a standard DIN A4 paper, which is 21 cm ×29.7 cm, and that the width of a banknote is 7 cm.

The maximum detection width obtainable with a single emitter and receiver in the frequency range of 20 to 30 GHz is about 1 cm to 1.5 cm. It is not possible to detect with one single linear scanning movement the presence of banknotes having stainless steel fibres incorporated therein, since proper positioning of the banknote, e.g. in the longitudinal direction and somewhat remote from the course of the emitter and receiver could avoid detection. Taken the above example of the A4 scanning area and assuming that the banknote has stainless steel fibres spread over its whole volume and assuming that the scanning movement is done in the longitudinal direction of the A4 scanning area, four sensors would be sufficient to detect all possible positions of a banknote. Security documents having smaller linear dimensions (e.g. credit cards), or security documents having only in a part of it stainless steel fibres incorporated, or a scanning area being larger than a DIN A4 document would require more sensors.

Figure 2:
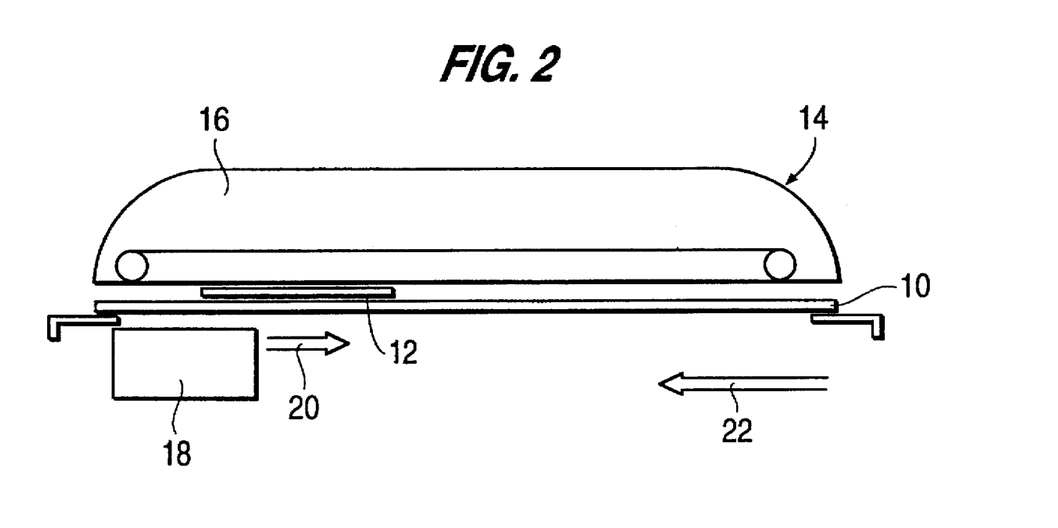
FIG. 2 gives a cross-sectional view of the relevant parts of a copying apparatus.

FIG. 2 illustrates in cross-section the parts of a photocopying apparatus 14 which are relevant for the present invention. The photocopying apparatus 14 comprises a platen glass 10 whereupon the documents 12 to be copied are positioned. A cover 16, e.g. an auto document feeder (ADF) cover may be provided above the platen glass 10. Scanning means 18 are provided under the platen glass 10 and perform one or more scanning movements immediately before and during the copying process.

Scanning speeds in direction of arrow 20 usually range from 100 to 300 mm/s, e.g. from 150 to 250 mm/s. The detection of the presence of stainless steel fibres in security documents should be preferably done at the same scanning speeds, thus without decreasing the scanning speed.

The return speeds of the scanning means 18 in the direction of arrow 22 are much higher, and are up to 1000 mm/s and even to 1600 mm/s and more. So the additional microwave system for the detection of stainless steel fibres should add as little as possible weight to the scanning means. The total weight of the scanning means 18 with inclusion of a microwave system should be preferably limited in the range of 400 to 600 g.

FIRST EMBODIMENT

A first microwave system for detecting the presence of stainless steel fibres in documents on the scanning area can be embodied as follows: an array of e.g. four independent working transceivers. Each transceiver has a Gunn diode working as a microwave source, a sensor head which includes the function of emitter and receiver and which substantially functions as an open-ended waveguide for the transceiver, and a detector diode, such as a Shottky diode or a point contact diode, providing a very fast DC voltage response. The transceivers are divided over the width of the scanning area. The output signals of the four detector diodes can be connected in an OR circuit which produces an 'on' signal in case at least one of the transceivers detect the presence of stainless steel fibres. This first system has, however, the drawback that four Gunn diodes are needed, which increases the cost and also the weight of the microwave system.

SECOND EMBODIMENT

Figure 3A:
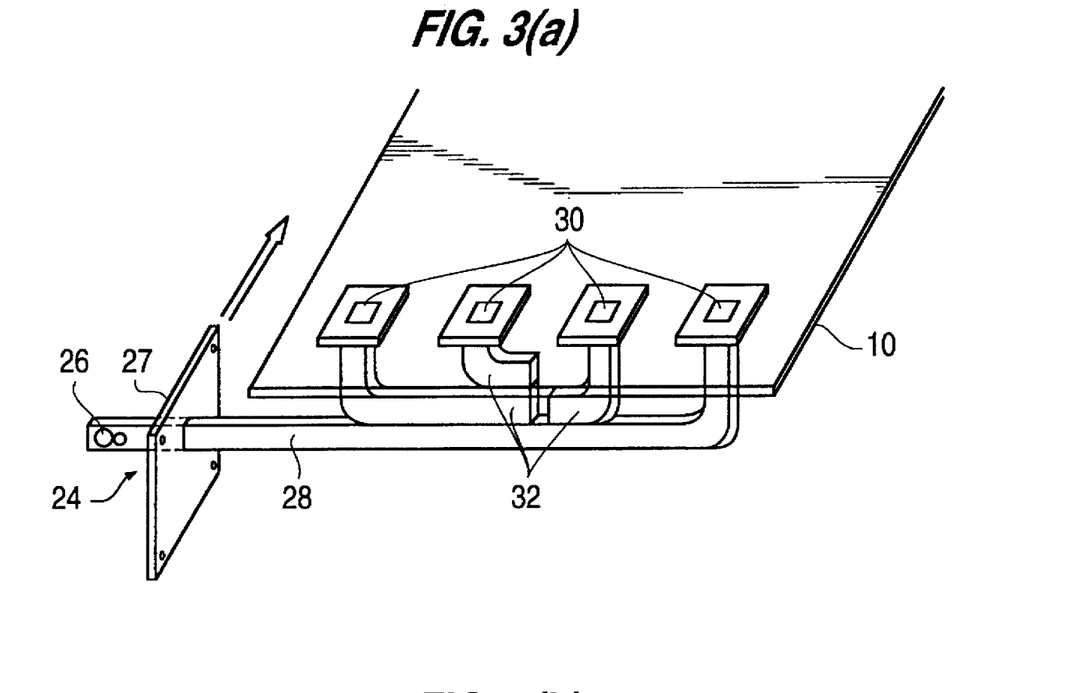
FIG. 3(a) illustrates an embodiment of a microwave system using directional couplers.
Figure 3B:
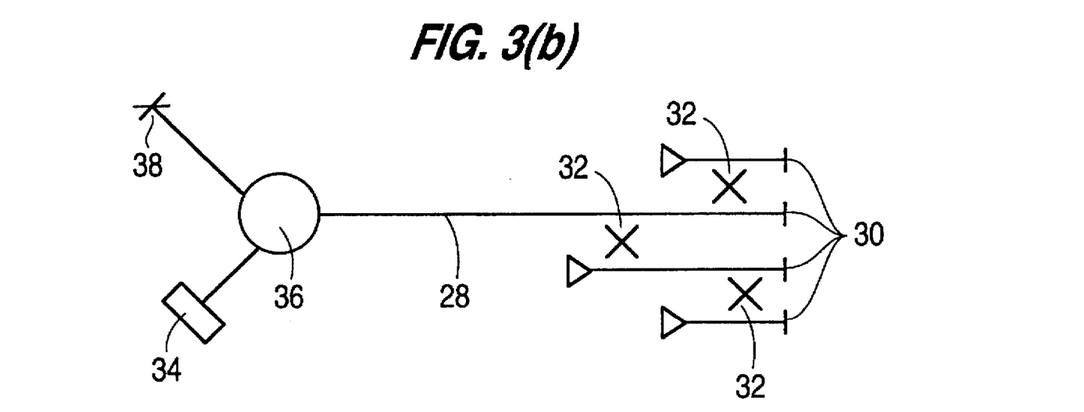
FIG. 3(b) gives a schematic representation of the microwave system illustrated in FIG. 3(b)

In order to reduce the cost and the weight of the microwave system a second microwave system may be designed where only one transceiver is used for an array of, for example, four sensors heads. FIGS. 3(a) and 3(b) illustrate such a microwave system 24. One transceiver 26 is connected by means of bolts and a flange 27 to a waveguide 28 with four sensor heads 30. Directional couplers 32, e.g. hybrid 3 dB couplers, positioned at the small sides of the waveguide are used to divide the power over the sensor heads. The transceiver 26 is basically constituted by a Gunn diode 34, a circulator 36 and a detector diode 38.

A flange 27 is not necessary. In order to reduce the volume and the weight of the microwave system it can be omitted and the wave guide 28 can be directly welded on the transceiver 26. Although having as advantage that only one Gunn diode and only one detector diode is used, this second microwave system has a number of drawbacks.

A first drawback is that due to the division of the available power and due to losses in the directional couplers as a consequence of the use of high frequencies, only a fraction of the generated power is available at the sensor heads, and, consequently, only a fraction of a fraction of the generated power can be reflected by the stainless steel fibres and become available at the detector diode. This may lead to the necessity of more powerful and thus more expensive Gunn diodes, to other decision algorithms in the signal processing or to more complex electronics.

A second drawback is that, if a waveguide structure is used to transmit the microwaves, the use of directional couplers can lead to a rather complex construction as shown in FIG. 3(a), which requires expensive machining or casting and which is no longer very compact and not light weight. This drawback may be solved by using e.g. microstrips as transmission media.

THIRD EMBODIMENT

Figure 4A:
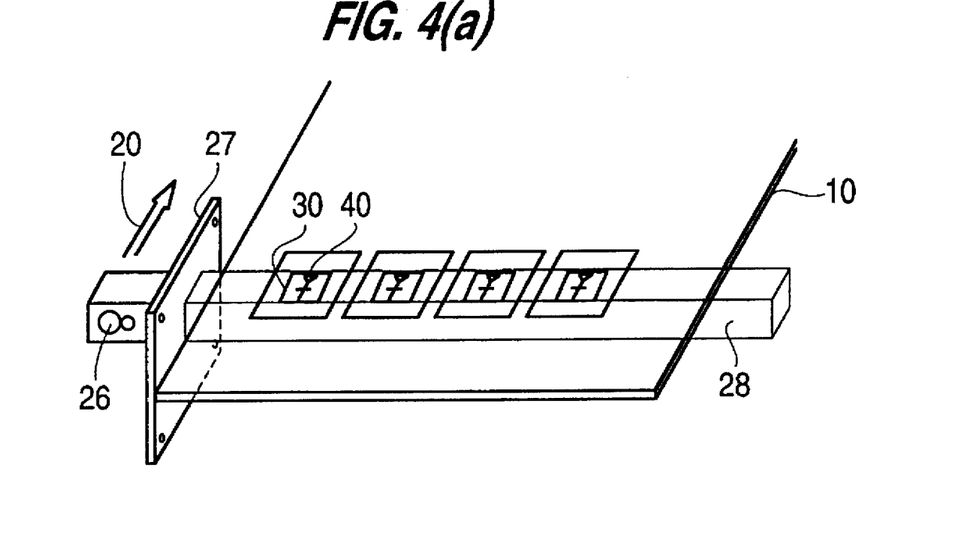
FIG. 4(a) illustrates an embodiment of a microwave system using switching diodes.
Figure 4B:
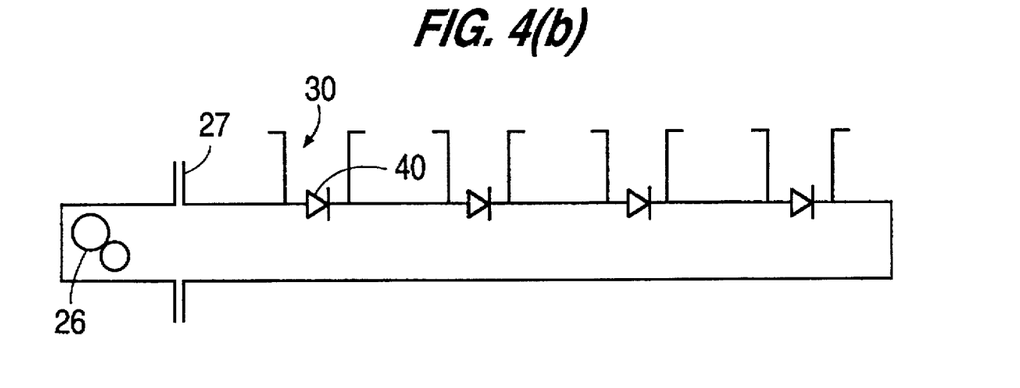
FIG. 4(b) gives a schematic representation of the microwave system illustrated in FIG. 4(a)
Figure 4C:
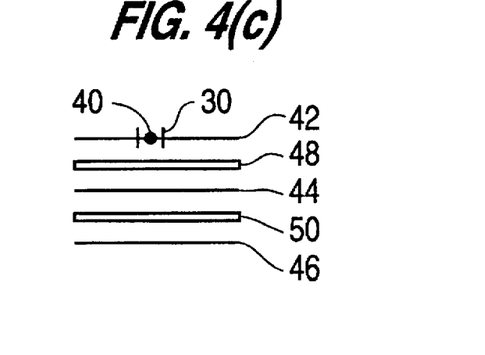
FIG. 4(c) gives a schematic representation of the cross-section of a microstrip alternative of the microwave system illustrated in FIG. 4(a)

A third microwave system which has a design which is straight forward and which provides a solution to the problem of the power division of the second microwave system, has been illustrated in FIGS. 4(a), 4(b) and 4(c).

Referring to FIGS. 4(a) and 4(b), the sensor heads 30, if of a proper dimension, function together with the waveguide 28 as an open ended transmission line. Switching diodes or PIN diodes 40, which are known as such in the art, are positioned at each sensor head 30 and can be used to short-circuit all but one of the sensor head 30, so that the entire power generated by the transceiver 26 is available at the one sensor head which is still open. The switching diodes 40 can be switched on and off periodically or sequentially so that each of the four sensor heads 30 is connected somewhat less than 25% of the time, taking into account a small dead time for each switching. The switching can be done synchronously with the clock frequency of a microprocessor, e.g. at 25 MHz.

If a waveguide structure 28 is used, the sensor heads can be located in the small wall of the waveguide. A very light waveguide with dimensions of about 10 mm by 5 mm and made of aluminium is very suitable for the building in a photocopying apparatus.

FIG. 4(c) schematically illustrates a transversal cross-section of a microstrip alternative. The microstrip is basically constituted by a central conductor strip 44 which is placed between two dielectric layers 48, 50 and two outer conductors 42 and 46. Suitable sensor heads or windows 30 can be made in one outer conductor 42 and a switching diode 40 can be placed across this sensor head 30. Having regard to the high frequencies used, teflon or similar material can be used for the dielectric layers 48, 50 in order to reduce the dielectric losses. Microstrips have the advantage of allowing cheap mass production and of providing a microwave system which can be easily integrated in existing copying apparatus. When using microstrips, a waveguide transition for the transducer is necessary or a more expensive transducer in microstrip must be used.

FOURTH EMBODIMENT

Figure 5A:
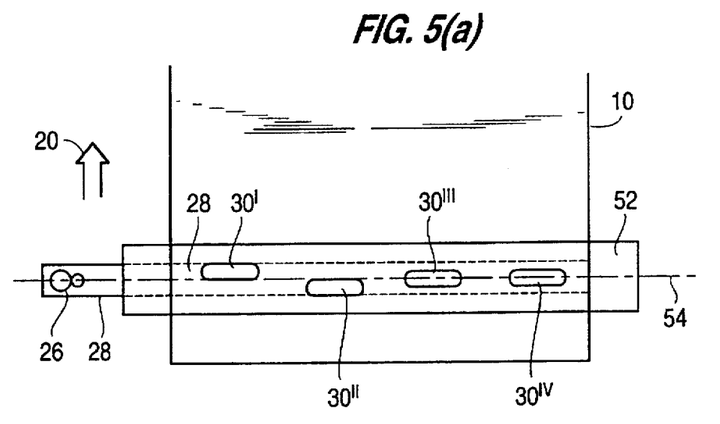
FIG. 5(a) illustrates a microwave system making use of resonant slots.
Figure 5B:
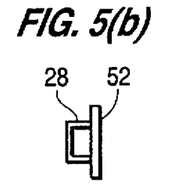
FIG. 5(b) gives a cross-section of the microwave system of FIG. 5(a) according to the line V—V.

A fourth microwave system has been depicted on FIGS. 5(a) and 5(b). It makes use of the so-called technique of resonating structures which take in case of a waveguide the form of resonant slots. This technique is known as such in the field of radar antennas for transmission over large distances.

The resonant slots are formed by the sensor heads 30 on the broad side of the waveguide 28 in a metal strip 52 with a width of about 20 mm which is connected to the waveguide 28.

Proper design and positioning of the slots 30 over the width of the waveguide will divide the generated power equally over the four slots $30^i$, $30^{ii}$, $30^{iii}$ and $30^{iv}$. The length of each slot 30 is about half a wavelength. The slot $30^i$ which is positioned nearest to the transceiver 26 is positioned away from the center line 54 in order to avoid that all generated microwave power would disappear through this slot $30^i$. Correct positioning of the first slot $30^i$ away from the center line makes that 25% of the generated microwave power is available at this first slot $30^i$ and that 75% of the generated microwave power passes the slot $30^i$. In order to make also 25% of the generated microwave power available at the second slot $30^{ii}$, this second slot $30^{ii}$ is positioned somewhat nearer to the center line 54 than the first slot $30^i$, since only 75% of the generated power is available. 50% of the generated microwave power passes the second slot $30^{ii}$ and in order to make also 25% of the generated microwave power available at the third slot $30^{iii}$, this third slot $30^{iii}$ is positioned still somewhat nearer to the center line 54 than the second slot $30^{ii}$, since here only 50% of the generated power is available. Only 25% of the generated microwave power passes the third slot $30^{iii}$, which makes that the fourth slot $30^{iv}$ should be positioned on the center line 54 in order to make this remaining power available at the fourth slot.

Correct positioning of the four slots 30 over the length of the wave guide 28 avoids that the power reflected through one slot does not disappear through the other slots but is transmitted until the transceiver 26.

The dimensions of the waveguide 28 are very limited for the applied frequency range (about 10 mm×about 5 mm), as a consequence a very small, compact and light structure can be obtained.

In case the waveguide 28 of FIGS. 5(a) and 5(b) is replaced by a stripline or microstrip, the resonating structures can be formed by so-called patch antennas placed on a dielectricum of the microstrip or stripline. These patch antennas are formed by small electrically conducting plates.

A number of alternative configurations are possible with this fourth system.

If the number of sensor heads increases, a slotted waveguide can be used both ends of which can be connected to a transceiver. Each transceiver can then feed only part of the number of sensor heads.

The technique of the resonant slots can also be combined with the technique of the switching diodes in order to avoid the problems connected with the division of power.

FIFTH EMBODIMENT

In a fifth microwave system use can be made of transceivers which have means such as a varactor for electronically tuning the frequency in function of a determined input voltage. Such varactors are currently available on the market. For example, the frequency can change from 24 GHz to 25.5 GHz for a voltage change of 3 V (volt). A first resonant slot in the waveguide can be designed to respond to a frequency of 24 GHz (0 V), a second slot to 24.5 GHz (1V), a third slot to 25 GHz (2 V) and a fourth slot to 25.5 GHz (3 V). In this way each sensor is sequentially active during the time its frequency is generated and full reflected power is available during this time. This technique is often called frequency multiplexing.

SIXTH EMBODIMENT

According to a sixth microwave system, the array of sensor heads can be designed in a way that the array loads a resonating structure such as a cavity resonator. The transceiver feeds its power into the cavity via a coupling device such as an iris. The power gets lost in the cavity and through the sensor heads. The presence of a stainless steel fibre passing in the detection field of one of the sensor heads will detune the cavity resonator, which can be easily observed by the detector diode since all power becomes available for the detector diode. This sixth system has the advantage of requiring only simple electronics, of working with only one frequency, of possible provision of a lightweight system and of a possible presence of a lot of sensor heads.

The difference with the fourth system is that in the fourth system each slot functions as a resonating structure on its own while in this sixth system the waveguide as a whole with inclusion of all its slots functions as a resonating structure.

SEVENTH EMBODIMENT

Figure 6A:
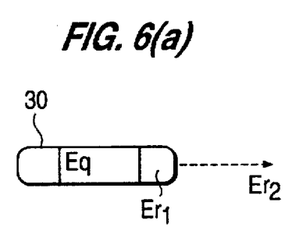
FIG. 6(a) gives a schematic representation of a conventional slot in a waveguide.
Figure 6B:
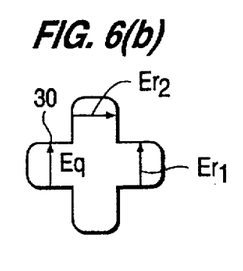
FIG. 6(b) and FIG. 6(c) give schematic representations of slots where use can be made of the technique of depolarization.
Figure 6C:
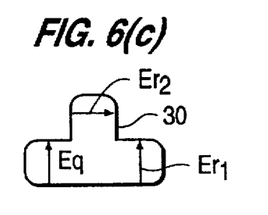

In yet another and seventh microwave system use can be made of the technique of depolarizations. Referring to FIG. 6(a), the generated electric field $E_g$ has always its orientation parallel to the small side of the sensor head 30, a stainless steel fibre will, supposing its orientation in the security documents is at random, not only reflect an electric field $E_{r1}$ component which is parallel to the generated electric field $E_g$ but also reflect an electric field $E_{r2}$ component which is perpendicular to the generated electric field $E_g$. If no measures are taken, the electric field component $E_{r2}$ is lost for detection purposes. The sensor windows 30 can now be designed in such a way that the reflected field component $E_{r2}$ is also received for detection purposes. FIGS. 6(b) and 6(c) show two possible embodiments of such a sensor head 30.

The electric field component $E_{r1}$ can now be collected in the same transmission system as the one for the generated electric field $E_g$ and the electrical field component $E_{r2}$ can be collected in another transmission system which is decoupled and which is adapted for another polarization system. This depolarization technique, which is known as such in radar applications, may allow for higher powers available at the detector diode.

EIGHTH EMBODIMENT

Figure 7A:
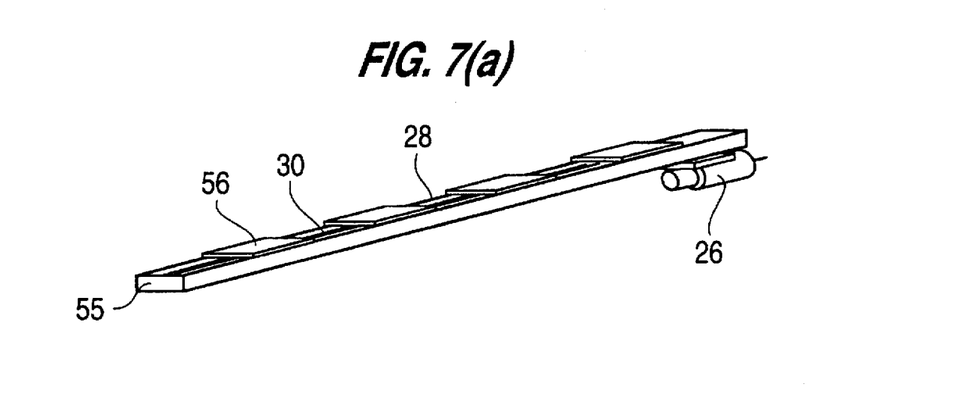
FIGS. 7(a) and 7(b) illustrate a single-source multi-detector system.

FIG. 7(a) illustrates an eighth embodiment which is a single-source multi-detector system. A single source 26, e.g. a Gunn-diode, generates microwaves which are transmitted in the waveguide 28 to four sensor heads 30 which take the form of slotted apertures in one of the sides of the waveguide 28. Preferably, each of the sensor heads is positioned from the source 28 at an integer number of times half the wavelength of the waves in the guide in order to optimize the available energy at the sensor heads 30. The end of the wave guide 55 is positioned from the nearest sensor head 30 at an uneven and integer number of times a quarter of the wavelength of the waves in the guide in order to maximize the available standing wave in the waveguide. A detector module 56 is positioned close to each sensor head 30. This detector module 56 is a small printed circuit board which is fixed to the waveguide 28.

Figure 7B:
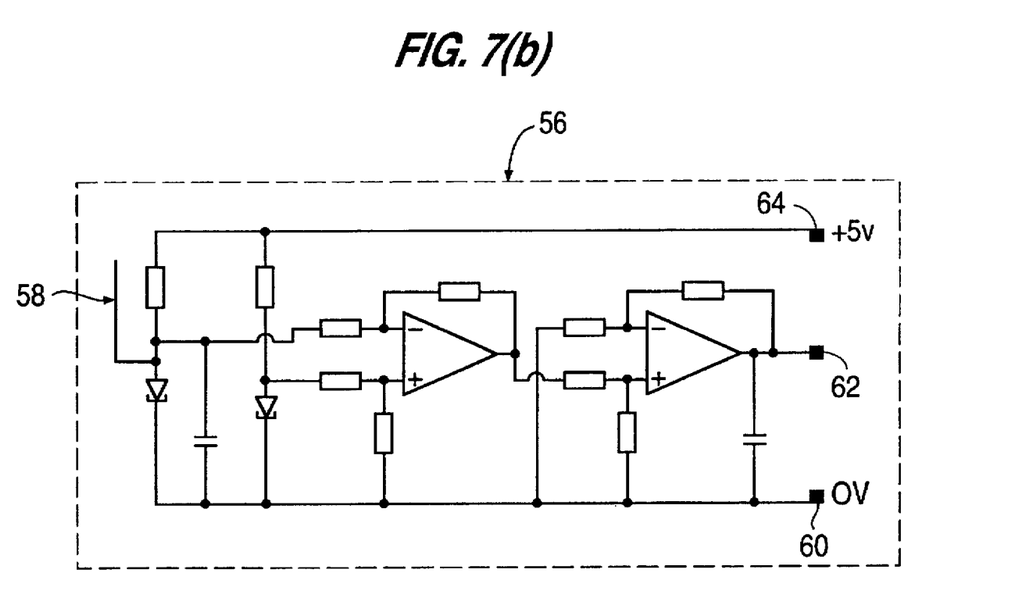

FIG. 7(b) shows a more detailed and enlarged view of such a detector module 56. Its real dimensions can be about 8 mm×30 mm. Reflected microwaves are received at antenna 58. The voltage signal of these reflected microwaves is amplified by the printed circuit and is available as an output signal between connection points 60 and 62. The detector module 56 is fed by a direct voltage of 5 V at point 64. The output signals provided by the four detector modules 56 are individually processed and the four outcome signals of this processing are led to a logical OR-circuit.

It will be clear for a man skilled in the art of microwave techniques that still other microwave systems can be conceived and designed. For example, different angled antennas can be designed as sensor heads for polarisation detection of the reflected signal.

Due to the fact that the detection of the present system is only based on the reflection of microwaves, care must be taken that the pattern of reflected microwaves is not disturbed by any electrically conducting material in the neighbourhood of the scanning area.

Tuning of the microwave system by means which are convenient in the field of microwaves, however, can make that the detection is not based on the absolute reflection level, but on a relative reflection level. This makes the system less critical.

Moreover, steel fibres, and specifically stainless steel fibres, have in the context of this invention a very small concentration in the base material, e.g. smaller than 5% by weight, and preferably smaller than 0.5% by weight. Due to this small concentration and due to the high reflection rate, the microwaves almost detect the individual fibre within the base material, which means that a response signal with a wide varying range can be obtained which allows to differentiate from ambient influences.

This wide varying signal can lead to very simple decision algorithms which can be based on calculating the standard deviation or the variance of the microwave reflection over at least a part of the document. Such a decision algorithm is robust in a sense that it can be applied in different copying apparatus, e.g. copying apparatus with different kinds of covers.

In case the calculated value of the algorithm exceeds a critical level, the presence of individual fibres in the document is detected and an 'on' signal can be produced. In case the calculated value remains below a critical level, no individual fibres are detected and an 'off' signal is produced.

In spite of the above-mentioned particular advantageous characteristics of the individual stainless steel fibres, particular care must be taken to the cover of the photocopying machine which may contain an inner reflecting surface which is often made of electrically conducting material and to the metallic parts of an ADF cover.

A solution to the first problem of the inner surface of the cover is found by using an inner surface which is light reflecting but which is of such a small degree of electrical conductivity that microwaves are not substantially reflected. The inner surface of the cover facing the platen 10 can be formed by e.g. a very thin sputtered metallic foil, a foil covered with an aluminium coating applied by chemical vapour deposition, a metallic lacquer or a metal sheet covered on its free underside with a dielectric transparant layer.

Another solution is to use a microwave absorbing inner surface, e.g. by carefully positioning at least two conductive layers parallel to one another.

Yet another solution to the first problem can be explained as follows. It is possible to tune the microwave system in such a way that the sensor heads or sensor windows receive a maximum response signal for any present stainless steel fibre while any electrically conductive plate such as a metal plate does not give a response signal by reason of its proper positioning with respect to the sensor heads or sensor windows: the tuning can be such that a maximum response is obtained at any distance which is an uneven multiple of a quarter wavelength, this is the proper place to position the security documents; at any even multiple of a quarter wavelength a minimum response is obtained, this is the place to position any present, electrically conductive plate.

A possible solution to the second problem of the ADF cover is found to incorporate into the belt of such an ADF cover a metallic foil or a foil covered with an aluminium coating applied by chemical vapour deposition, or a metallic lacquer in order to shield against any ambient reflections.

The above problems of the inner reflecting surface and of the ADF cover can also be overcome by the use of more complex decision algorithms which can be implemented in hardware or in software or in a combination of both. Generally, these decision algorithms may include following modules:

- a module which differentiate between a fibre and a metal plate: if the continuous and constant presence of an electrically conductive material is detected over a predetermined distance, this material is identified as a metal plate and not as fibres;
- a module which determines the size of electrically conductive materials; if this size is much smaller than the size of that part of the documents which are expected to comprise fibres, the material is not identified as fibres but as e.g. a metal staple used to holding documents together;
- a module which detects fibres and which comprises a bandpass filter to filter out the frequency range of a typical response generated by the fibres.

We claim:

1. A reproduction apparatus for reproducing documents which comprise a base material, said apparatus comprising:

a reproduction platen located in a microwave scanning area for positioning a document comprising a base material on one side of said platen;

scanning means for scanning the scanning area, said scanning means being positioned on one major side of said platen;

means for obtaining relative movement between said scanning means and the document in order to allow for said scanning, said scanning means comprising a microwave system for detecting the presence in said base material of particles having electromagnetic properties which are substantially different from electromagnetic properties of said base material, said particles being capable of functioning as electrical dipoles, said microwave system comprising a number of microwave sources for generating microwaves, a number of microwave emitters for emitting microwaves to the scanning area, a number of microwave receivers for receiving only microwaves which are reflected, and a number of microwave detectors for detecting only reflected microwaves, the number of microwave emitters and the number of microwave receivers being respectively greater than the number of microwave sources, and being respectively greater than or equal to the number of microwave detectors, the position and number of the microwave emitters and the microwave receivers being such that said number of microwave detectors detect the presence of particles functioning as electrical dipoles and being incorporated in at least a part of the base material of the document, irrespective of the position and size of the document in the scanning area.

2. An apparatus according to claim 1 wherein the number of microwave sources is equal to one.

3. An apparatus according to claim 2, wherein the microwave emitters are arranged in an array.

4. An apparatus according to claim 1, the apparatus further comprising means for guiding microwaves between the microwave sources and the microwave emitters, and whereby said means for guiding microwaves are formed by a stripline, a microstrip or a slotline.

5. An apparatus according to claim 1 wherein the weight of the microwave system is less than 100 g.

6. An apparatus according to claim 1 wherein the apparatus further comprises means for processing any signal produced by the reflected microwaves.

7. An apparatus according to claim 3 wherein the microwave system further comprises for each microwave emitter a switching diode so arranged that it can short-circuit the corresponding microwave emitter.

8. An apparatus according to claim 3 wherein the microwave emitters are arranged as resonating structures responding to one single frequency.

9. An apparatus according to claim 3 wherein each of the microwave emitters responds to one single resonant frequency which is different from the resonant frequency of the other microwave emitters and wherein the microwave system further comprises means for electronically tuning the frequency of the generated microwaves so that by generating microwaves with changing frequency each microwave emitter becomes sequentially active.

10. An apparatus according to claim 3 wherein the array of microwave emitters loads a resonating structure like a cavity resonator.

11. An apparatus according to claim 3 wherein the microwave system comprises two transmission systems, one transmission system for transmitting the generated microwaves and reflected microwaves in one polarization, and another transmission system, being decoupled from said one transmission system for transmitting reflected microwaves in a polarization system which is different from or equal to the polarization system of the generated microwaves.

12. An apparatus according to claim 3, wherein the number of microwave receivers and the number of microwave detectors is equal to the number of microwave emitters.

13. A reproduction apparatus for reproducing documents which comprise a base material, said apparatus comprising:

a platen for forming a scanning area and for positioning the documents on one side thereof;

scanning means for scanning the scanning area, said scanning means being positioned on one side of said platen;

means for obtaining a relative movement between the scanning means and the documents in order to allow for said scanning, said scanning means comprising a microwave system for detecting the presence in said base material of particles having some electromagnetic properties which are substantially different from the corresponding electromagnetic properties of said base material, said microwave system comprising a number of microwave sources for generating microwaves, a number of microwave emitters for emitting microwaves to the scanning area, a number of microwave receivers for receiving microwaves which are reflected, and a number of microwave detectors for detecting the reflected microwaves, the number of microwave emitters, the number of microwave receivers and the number of microwave detectors being greater than or equal to the number of microwave sources, the position and number of the microwave emitters and the microwave receivers being such that they can detect the presence of particles having some electromagnetic properties which are substantially different from the corresponding electromagnetic properties of the base material and being incorporated in at least a part of the base material of the documents, irrespective of the position and size of the documents on the scanning area, and wherein the microwave system further comprises for each microwave emitter a switching diode so arranged that it can short-circuit the corresponding microwave emitter.

14. An apparatus according to claim 13, wherein the microwave emitters are arranged as resonating structures responding to one single frequency.

15. An apparatus according to claim 13, wherein each of the microwave emitters responds to one single resonant frequency which is different from the resonant frequency of the other microwave emitters and wherein the microwave system further comprises means for electronically tuning the frequency of the generated microwaves so that by generating microwaves with changing frequency each microwave emitter becomes sequentially active.

16. An apparatus according to claim 13, wherein the array of microwave emitters loads a resonating structure like a cavity resonator.

17. A reproduction apparatus for reproducing documents which comprise a base material, said apparatus comprising:

a platen for forming a scanning area and for positioning the documents on one side thereof;

scanning means for scanning the scanning area, said scanning means being positioned on one side of said platen;

means for obtaining a relative movement between the scanning means and the documents in order to allow for said scanning, said scanning means comprising a microwave system for detecting the presence in said base material of particles having some electromagnetic properties which are substantially different from the corresponding electromagnetic properties of said base material, said microwave system comprising a number of microwave sources for generating microwaves, a number of microwave emitters for emitting microwaves to the scanning area, a number of microwave receivers for receiving microwaves which are reflected, and a number of microwave detectors for detecting the reflected microwaves, the number of microwave emitters, the number of microwave receivers and the number of microwave detectors being greater than or equal to the number of microwave sources, the position and number of the microwave emitters and the microwave receivers being such that they can detect the presence of particles having some electromagnetic properties which are substantially different from the corresponding electromagnetic properties of the base material and being incorporated in at least a part of the base material of the documents, irrespective of the position and size of the documents on the scanning area, and wherein the microwave system comprises two transmission systems, one transmission system for transmitting the generated microwaves and reflected microwaves in one polarization, and another transmission system, being decoupled from the first transmission system for transmitting reflected microwaves in a polarization system which is different from or equal to the polarization system of the generated microwaves.

18. An apparatus according to claim 17, wherein the number of microwave receivers and the number of microwave detectors is equal to the number of microwave emitters.

* * * * *